United States Patent [19]

Hepler, Jr.

[11] Plant 4,014

[45] Feb. 1, 1977

[54] PEACH TREE

[75] Inventor: Mrs. Alexander B. Hepler, Jr., Long Beach, Calif.

[73] Assignee: L. E. Cooke Co. Inc., Visalia, Calif.

[21] Appl. No.: 674,049

[22] Filed: Apr. 5, 1976

[51] Int. Cl.[2] ..... A01H 5/03

[52] U.S. Cl. ..... Plt./43

[58] Field of Search ..... Plt./43

*Primary Examiner*—Robert E. Bagwill

CLAIM

A new and distinct variety of peach tree, substantially as illustrated and described, characterized by a hardy, vigorous, well foliaged and productive tree producing fruit of good size, color and eating quality and further characterized by the ability of the tree to grow satisfactorily and produce regular, annual crops with substantially less winter chilling requirement than other similar varieties such as Elberta and Hale type peaches; the variety is further characterized by ease of propagation by usual nursery methods.

1 Drawing Figure

1

The present invention relates to a new and distinct variety of hardy, vigorous, well foliaged and productive peach tree of the freestone type; the variety being primarily characterized—as to novelty—by its ability to set and mature a satisfactory crop of fruit with considerably less winter chilling than other similar varieties, the fruit of the present variety being similar to the regular Elberta peach (not patented).

The variety is further characterized by:

Relatively early flowering habit with large pink flowers.

A tree (plant) which is vigorous, of spreading open habit, becoming quite large at maturity; the flowers, foliage and fruit being similar to the regular Elberta Peach.

A tree which grows and fruits satisfactorily even in areas which often do not have sufficient winter chilling weather to induce proper flowering and fruiting thus making this variety useful for planting in mild area such as portions of Southern California and other areas with similar winter chilling problem. This variety is especially desirable for home orchard planting.

The present variety of fruiting peach tree was originated by me in my home garden located at 3420 Valverde Ave., Long Beach, Calif. 90808, as a chance seedling which was grown from the seed of an Elberta peach.

Subsequent to origination of the variety it has been successfully asexually reproduced in the nursery of the L. E. Cooke Co., located at Visalia, Calif. 93277, 26333 Road 140 (between Ave. 256 and Ave. 248), by budding and grafting. Propagation was first made by taking grafting scions from the original tree, located as above, and working it on young Nemaguard (peach understock variety) seedlings; the reproductions having run true in all respects.

The color photograph illustrates the fruit and foliage of the variety.

Referring now specifically to the new and distinct variety of fruiting peach tree, the following is a detailed description thereof in outline; all major color plate identification being by reference to the British Colour Council Horticultural Colour Chart, except where common terms of color definition are employed.

Type: Hardy, large, vigorous, seedling, spreading.
Class—Type: Fruiting; freestone.

2

Flowers: Flower buds—size; large; medium length; conic. Flowers abundantly; flower size—large; color—pink; early (often blooming as early as February 18).

Fruit: Specimens described; as grown and observed at Visalia, Calif., August, 1975.

*Date of ripening.*—First picking—August 19, 1975; last picking—Aug. 30, 1975.

*Size.*—Large; diameter, axil 3¼"; transverse in suture plane 3⅛ inch.

*Form.*—Uniform; globose.

*Suture.*—Distinct; shallow; extends from base to beyond but discontinuous with slight depression beyond pistil point.

*Ventral surface.*—Rounded; lipped toward base on both sides; lips usually equal.

*Cavity.*—Rounded; elongated in suture plane with suture showing on one side; depth ⅝ inch; breadth ⅞ inch.

*Base.*—Rounded. Apex: short, depressed. Pistil point: Rather inconspicuous.

Skin: Medium thick; medium toughness; tenacious to flesh. Tendency to crack: none noted in either wet or dry weather. Color: yellow, similar to Orpiment Orange 10/2 or Apricot 609/1 with red overlay (see color illustrations). The red overlay may cover half or more than half of the skin surface. Down: moderate; quite short; does not roll up when rubbed.

Flesh: Color—yellow. Surface of pit cavity: red with pinkish fibers. Juice: moderately abundant; rich. Texture: firm; fine texture; crisp—meaty—melting.

Fibers: Few; fine; tender.

Flavor: Delicate; subacid.

Aroma: May be distinct to wanting.

Eating quality: Good to best.

Stone: Freestone; parts from flesh smoothly.

*Stone size.*—Similar to regular Elberta.

*Form.*—Globose. Base: straight to oblique.

*Sides.*—Equal.

*Surface.*—Irregularly furrowed throughout.

*Ridges.*—Rather jagged. Pits: elongated to angular.

*Ventral edge.*—May be thick to thin; usually without wing. Dorsal edge: full, with deep groove throughout. Ridges: Continuous. Color of stone: brownish. Tendency to split: slight tendency in wet season.

Use: Local market; desert; culinary; canning.

Keeping quality: Good. Shipping quality: good.

Resistance to insects, diseases: No unusual susceptabilities noted.

Adaptability to climatic conditions: The present variety of fruiting peach tree, while similar to its seed parent, Elberta, in general growth and tree habit and producing fruit similar to the Elbertas, differs in the winter chilling requirement. Whereas the Elberta and other similar varieties usually require from 800 to 1,000 hours chilling for vigorous growth and for fruit production the present variety will bear good crops of fruit with as little as 326 hours. Evidence cited for this: every minute of temperature below 45° (Fahrenheit) from November 1973 to May 1974 was tabulated by the United States Weather Bureau at Long Beach, Calif. The minimum chilling requirements for this variety are not yet known. However, in this particular year of testing and from 1972 to 1975 inclusive, the present variety has consistently fruited very heavily while Elberta and Hale (not patented) type peaches have fruited poorly or not at all in an area (Long Beach, Calif.) with so little winter chilling.

The peach tree and its fruit as herein described and illustrated may vary in slight detail due to climatic, soil and cultural conditions under which the variety may be grown: the present description being of the variety as grown at Visalia, Calif., and at Long Beach, Calif., its place of origin.

The following is claimed:

1. A new and distinct variety of peach tree, substantially as illustrated and described, characterized by a hardy, vigorous, well foliaged and productive tree producing fruit of good size, color and eating quality and further characterized by the ability of the tree to grow satisfactorily and produce regular, annual crops with substantially less winter chilling requirement than other similar varieties such as Elberta and Hale type peaches; the variety is further characterized by ease of propagation by usual nursery methods.

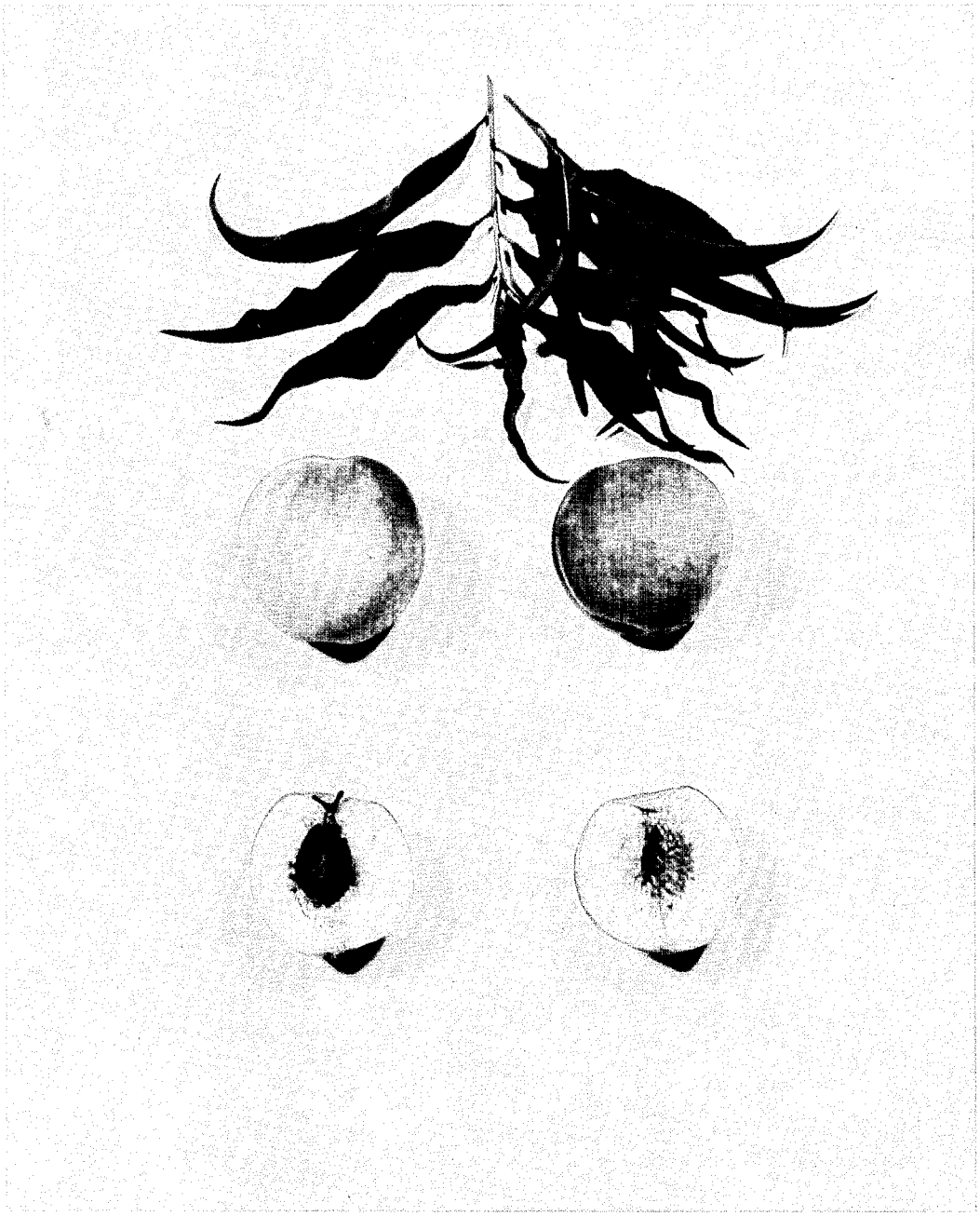

* * * * *